United States Patent
Sverzhin-Babiner

(10) Patent No.: US 9,271,816 B2
(45) Date of Patent: *Mar. 1, 2016

(54) MULTI-HEADED TOOTHBRUSH

(71) Applicant: Babiner Dental PC, Feasterville, PA (US)

(72) Inventor: Maxim Sverzhin-Babiner, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/825,027

(22) Filed: Aug. 12, 2015

(65) Prior Publication Data
US 2015/0342712 A1    Dec. 3, 2015

Related U.S. Application Data

(63) Continuation-in-part of application No. 14/617,664, filed on Feb. 9, 2015.

(60) Provisional application No. 61/965,882, filed on Feb. 7, 2014.

(51) Int. Cl.
| | | |
|---|---|---|
| *A61C 17/34* | (2006.01) | |
| *A46B 5/00* | (2006.01) | |
| *A61C 17/22* | (2006.01) | |
| *A61C 17/20* | (2006.01) | |
| *A46B 9/04* | (2006.01) | |

(52) U.S. Cl.
CPC ............. *A61C 17/349* (2013.01); *A46B 5/0012* (2013.01); *A46B 9/045* (2013.01); *A61C 17/20* (2013.01); *A61C 17/222* (2013.01)

(58) Field of Classification Search
CPC .... A61C 17/349; A61C 17/20; A61C 17/222; A46B 5/0012; A46B 9/045
See application file for complete search history.

(56) References Cited

U.S. PATENT DOCUMENTS

| | | | | |
|---|---|---|---|---|
| 1,110,406 | A * | 9/1914 | Schreck | A46B 7/06 15/201 |
| 5,673,454 | A * | 10/1997 | Quintanilla | A46B 5/0012 132/309 |
| 6,405,401 | B1 * | 6/2002 | Hellerud | A46B 9/045 15/167.1 |
| 7,757,330 | B2 * | 7/2010 | Hegemann | A61C 1/0092 15/22.1 |
| 8,590,092 | B2 * | 11/2013 | Dickie | A46B 5/0062 15/22.1 |

* cited by examiner

*Primary Examiner* — Shay Karls

(57) ABSTRACT

The present invention generally relates to oral hygiene. In particular, embodiments of the invention relate to a multi-headed toothbrush and method for brushing teeth.

20 Claims, 6 Drawing Sheets

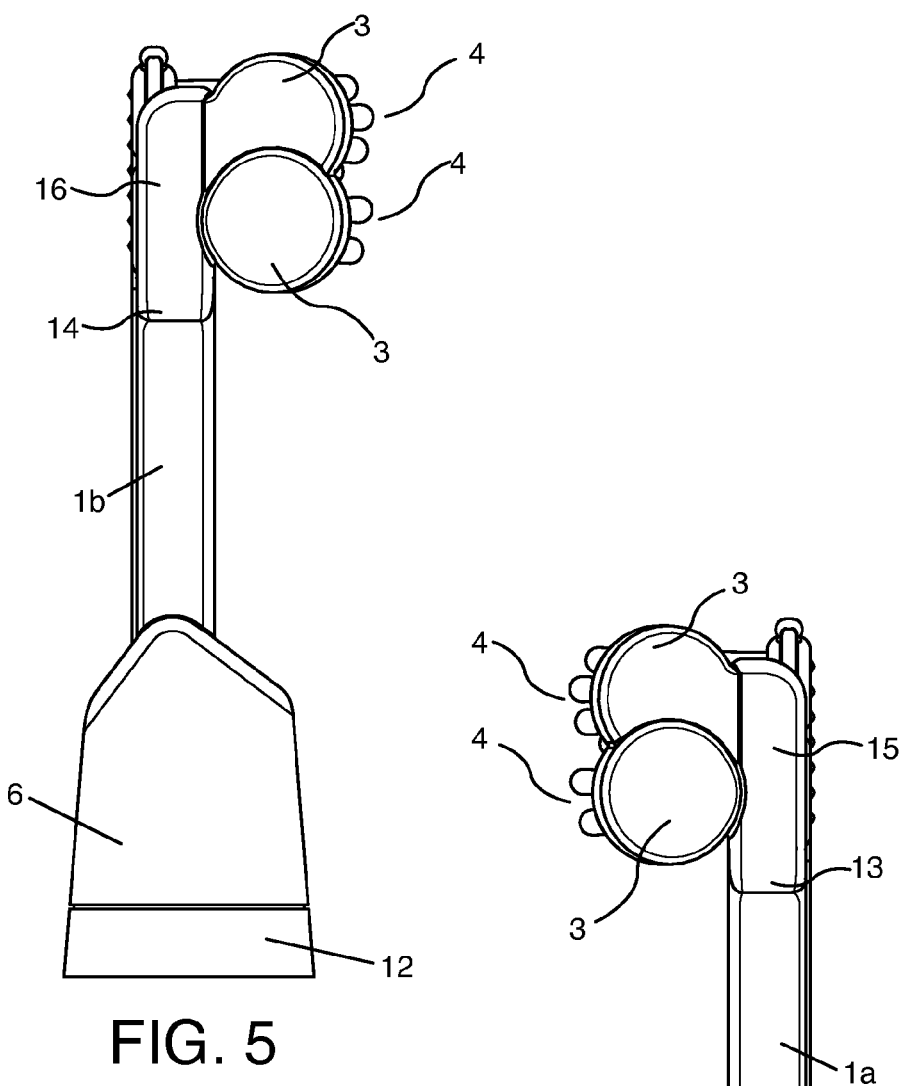

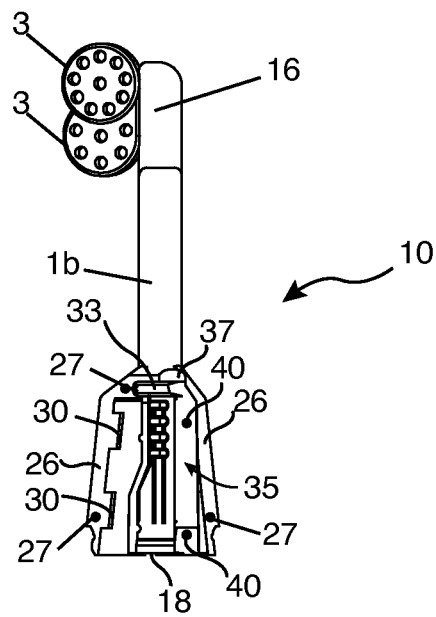
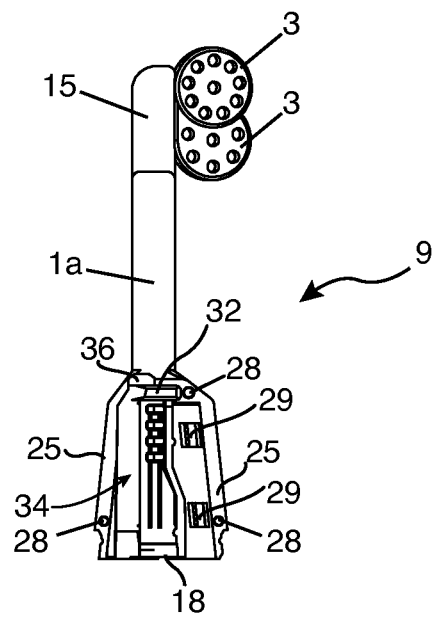
FIG. 10          FIG. 11
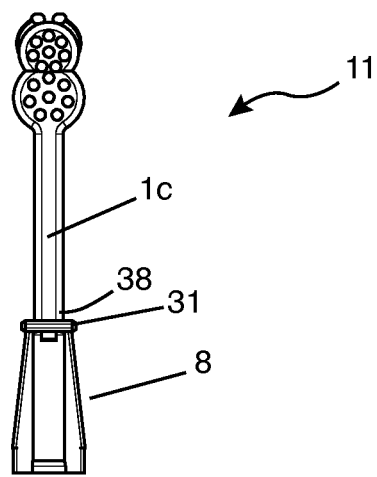
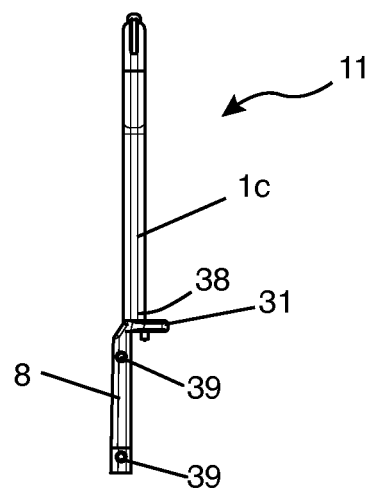
FIG. 12A          FIG. 12B

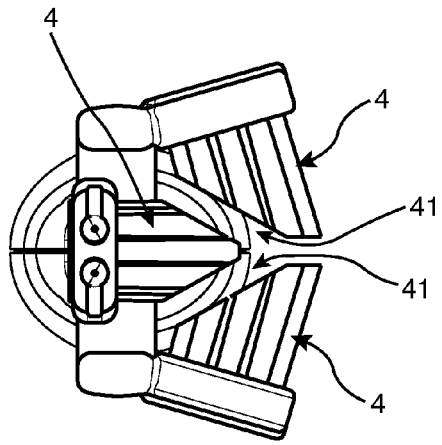
FIG. 13
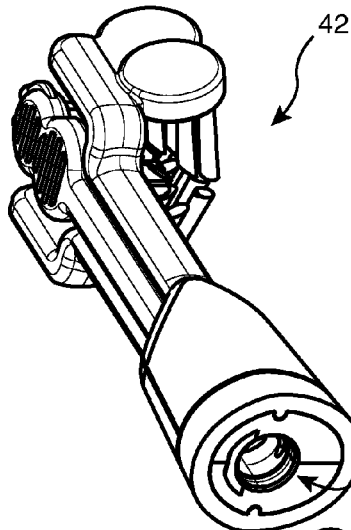
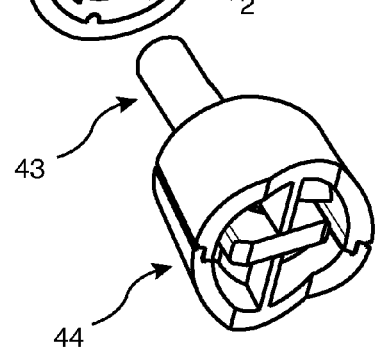
FIG. 14A
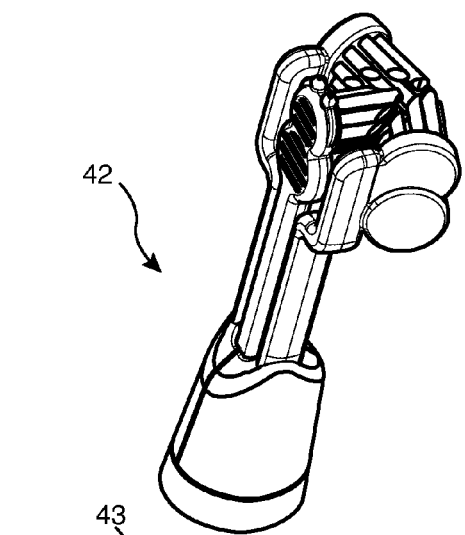
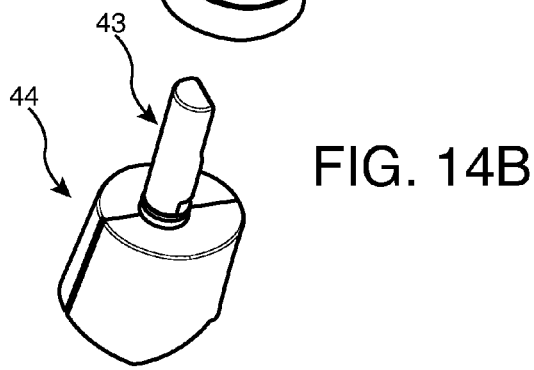
FIG. 14B

MULTI-HEADED TOOTHBRUSH

CROSS-REFERENCE TO RELATED APPLICATIONS

This application is a continuation-in-part of pending U.S. patent application Ser. No. 14/617,644, entitled "Multi-Headed Toothbrush", filed Feb. 9, 2015, currently pending, which claims the benefit of U.S. Provisional Application 61/965,882 entitled Multi-Headed Toothbrush, filed Feb. 7, 2014. The entire disclosures of the above-referenced applications are incorporated herein by reference in entirety for all purposes.

FIELD OF INVENTION

The present invention generally relates to oral hygiene. In particular, embodiments of the invention relate to a multi-headed toothbrush and method for brushing teeth.

BACKGROUND OF THE INVENTION

A known apparatus to brush teeth with multiple brush heads described in U.S. Pat. No. 5,673,454A involves the use of a three-headed brush that enables the user to accomplish brushing of all exposed sides of the user's teeth simultaneously. Disadvantageously, the rigid nature of such multi-headed brushes as the type disclosed in U.S. Pat. No. 5,673, 454A, do not conform to tooth and gum structures of different anatomical sizes and qualities, causing suboptimal pressure on teeth and gums.

Inventions in the prior art include a variety of improvements to the basic toothbrush such as a three-headed brush that touches three tooth faces simultaneously (U.S. Pat. No. 5,673,454A) to shorten the necessary brushing time by 3 times. Additionally, the invention disclosed in US 20120279002 A1, is a toothbrush that incorporates sonic oscillation technology to aid in the removal of plaque without a back and forth motion. No inventions in the prior art eliminate the problems of pinching the bodies of the mouth and gums while enabling the transmittal of sonic energy motion to a multi-headed toothbrush.

SUMMARY OF THE INVENTION

It has been left for the present inventor to discover a solution to the problem of pinching that is typically associated with three headed toothbrushes. It has also been left for the present inventor to discover a solution to the challenge of transmission of sonic energy through flexible materials included in a brush head.

At the heart of the present invention is a toothbrush with three heads that is able to be connected to a handle in such a way that they have the ability to flex independently of one another. This toothbrush also allows for the transfer of energy associated with sonic motion or other motion to the brush heads. In this way, vibration or other motion generated by a mechanism located the handle of the brush can be transferred to the brush head, reducing the amount of work that the user has to perform to clean his or her teeth. The invention still retains the benefits of multi-headed toothbrushing by allowing for teeth to be cleaned in a fraction of the time required to clean teeth while utilizing traditional single brush head methods, while avoiding the requirement for a user to perform a back and forth motion user dexterity and the pinching of mouth bodies typically associated with multi-headed toothbrushes.

In a preferred embodiment of the invention, the three brush heads form a single unit, each connected to one another through flexible attachment arms. In such embodiment, the three heads independently flex when pressure is applied to the teeth for a consistent pressure on each tooth independent of the shape of the tooth. For instance, in this preferred embodiment of the invention, consistent pressure is applied regardless of whether the tooth is a narrow tooth such as an incisor, or a wide tooth such as a molar.

In embodiments of the invention, the multi-headed brush head unit is able to connect to a variety of toothbrush handles that are known in the prior art as well as other items that could act as a toothbrush handle. In a preferred embodiment of the invention, sonic motion is generated with a motor in the handle and this motion transmits to the brush heads through independently flexing attachment structures. A preferred embodiment of the invention specifically uses DuPont® bristles.

BRIEF DESCRIPTION OF THE DRAWINGS

FIG. 5 View from left side of the preferred embodiment of the invention.

FIG. 6 View from right side of the preferred embodiment of the invention.

FIG. 10. View from the right side of a left component in certain embodiments of the invention.

FIG. 11. View from the left side of a right component in certain embodiments of the invention.

FIG. 12A. Frontal view of a center component in certain embodiments of the invention.

FIG. 12B. View from the left side of a center component in certain embodiments of the invention.

FIG. 13. Top-down view in a certain embodiment of the invention showing distance between bristles.

FIG. 14A. Bottom angular view of a portion of a handle fitting with an assembly in certain embodiments of the invention.

FIG. 14B. Top angular view of a portion of a handle fitting with an assembly in certain embodiments of the invention.

DETAILED DESCRIPTION OF CERTAIN EMBODIMENTS OF THE INVENTION

Figure 1:
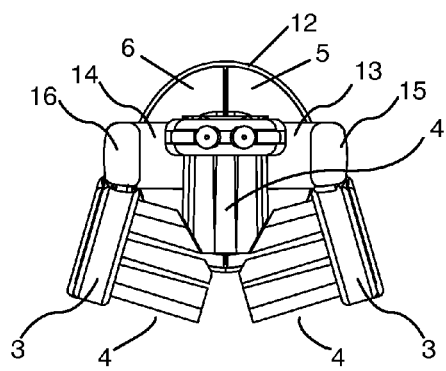
FIG. 1 Top-down view of the preferred embodiment of the invention.

The tooth brushing devices known in the prior art comprise a handle attached directly to a brush head. The handle is used to control the motion of the brush head. The brush head is used to directly dislodge plaque and debris from the teeth, gums, and other mouth structures. The simple versions of toothbrushes known in the prior art have a single head attached to a stiff, solid handle.

The handles of toothbrushes in the prior art are simple and made of plastic, wood, or other stiff material. The handle can be narrow, molded, simple, or complexly shaped. Alternatively, toothbrushes have a flexible neck region between the stiff handle and the brush head. Additional modifications include a motorized handle that provides a spinning action or sonic action to the bristles.

In the prior art, the bristles in a toothbrush head are arranged in various conformations. The simplest embodiment is a series of bristle clusters in a grid formation of three by ten. The bristle clusters can be variable in density and arrangement. Toothbrush bristles are either made of hard rubber or a toothbrush bristle material made exclusively by DuPont®. The preferred embodiment of the present invention uses the DuPont® bristles.

The common tendency for users to brush for 45 seconds instead of the 2 minute duration recommended by the American Dental Association results in teeth that are not sufficiently cleaned using a simple, single-head toothbrush. One improvement over the single-head toothbrush, and one that addresses this problem directly, is a three-headed toothbrush. A three-headed toothbrush (as in U.S. Pat. No. 5,673,454A) cuts the time of brushing by three because three faces of the teeth are brushed simultaneously. A three-headed toothbrush also solves the problem of focusing inadequate time on the palatal side of the tooth as people tend to focus on the buccal side instead. The three headed toothbrush forces a user to brush the lingual, buccal, and bite sides of the teeth equally.

Three headed toothbrushes need to apply pressure to the teeth as they brush, so that the bristles can remove material from multiple directions simultaneously. However, three-headed toothbrushes with stiff necks, such as that disclosed by U.S. Pat. No. 5,673,454A, are known to cause pinching of the gums and teeth, which can be painful or even damaging to mouth structures. The preferred embodiment of the present invention solves that problem via three-headed toothbrush containing a flexible neck region that attaches each head to the handle independently preventing excessive pressure and pinching. A simple toothbrush relies on the user to provide a physical back-and-forth action that requires skill and deft motor function of the arm and hands. A problem, therefore, that accompanies many tooth-brushing activities, is that children, the elderly, the disabled, and others who suffer limitations in motor function are limited in their ability to adequately clean their teeth with traditional tooth-brushing motions. The preferred embodiment of the present invention solves that problem by incorporating into its design a toothbrush with bristles that vibrate, spin, or provide sonic motion overcomes the need for the user to have dexterous control of the toothbrush.

As noted above, it remained for the present inventor to recognize that a combination of toothbrush improvements have never been present in the same device. Embodiments of the present invention incorporate the benefits of a three-headed toothbrush, flexible neck regions 1, and the capability to deliver sonic action through the bristles. The present inventor has discovered that the flexible neck region available in prior art prevented the transmission of sonic motion to the bristles. Embodiments of the present invention incorporate a rigid brush head material, such as plastic, in such a manner that allows the brush neck to flex with the contours of bodies of the mouth while still transmitting the energy necessary to facilitate the sonic motions of the brush. FIG. 5 and FIG. 6 disclose rounded heads 3 that incorporate means to transmit sonic or spinning energy to the bristles of the brush.

Figure 3:
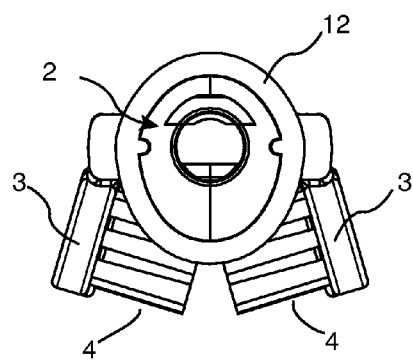
FIG. 3 Bottom-up view of the preferred embodiment of the invention.
Figure 2:
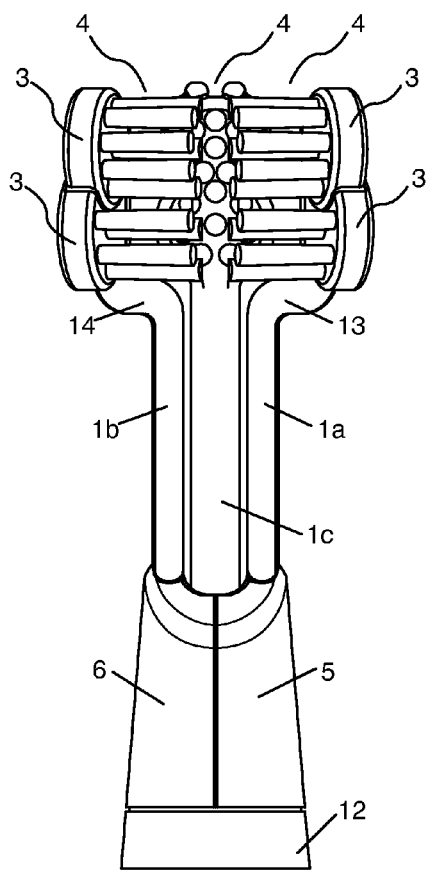
FIG. 2 Frontal view of the preferred embodiment of the invention.
Figure 4:
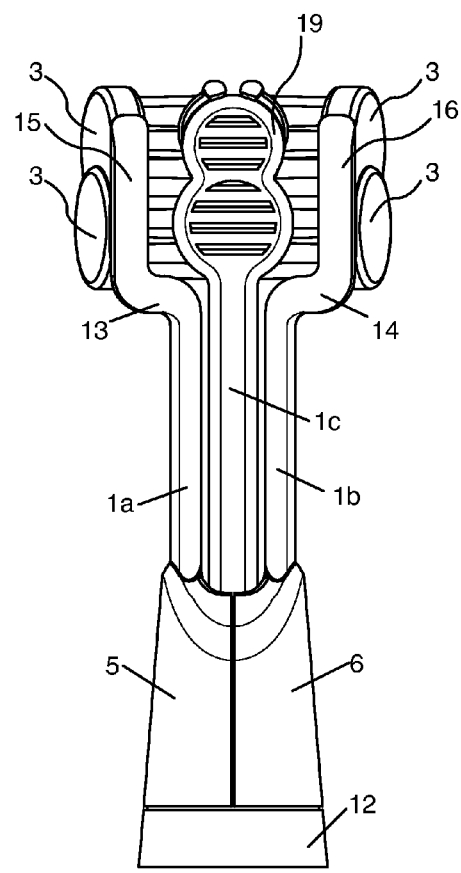
FIG. 4 Rear view of the preferred embodiment of the invention.

Embodiments of the present invention comprise only of a head and neck region that is removable from the handle. This allows for an economical change to a fresh toothbrush head when the bristles become worn. FIG. 3 discloses a cavity 2 incorporated into one embodiment of the invention showing a means to securely attach the embodiment of the invention to a brush head handle. Similarly, the head and neck unit of an embodiment of the present invention can be made to fit onto multiple types of handles.

A toothbrush embodying the principles of the invention can include a variety of bristle conformations. Such bristles can be long or short; they can be a uniform length, or variable in length. The inventor has noted that short bristles are effectively stiffer and the length of bristles can be used to vary the stiffness while using the same materials. In embodiments of the invention, bristles can be very dense or sparsely placed. In embodiments of the invention, each of the three heads can mirror the others in bristle length and conformation or the conformation can be different between heads.

Figure 8:
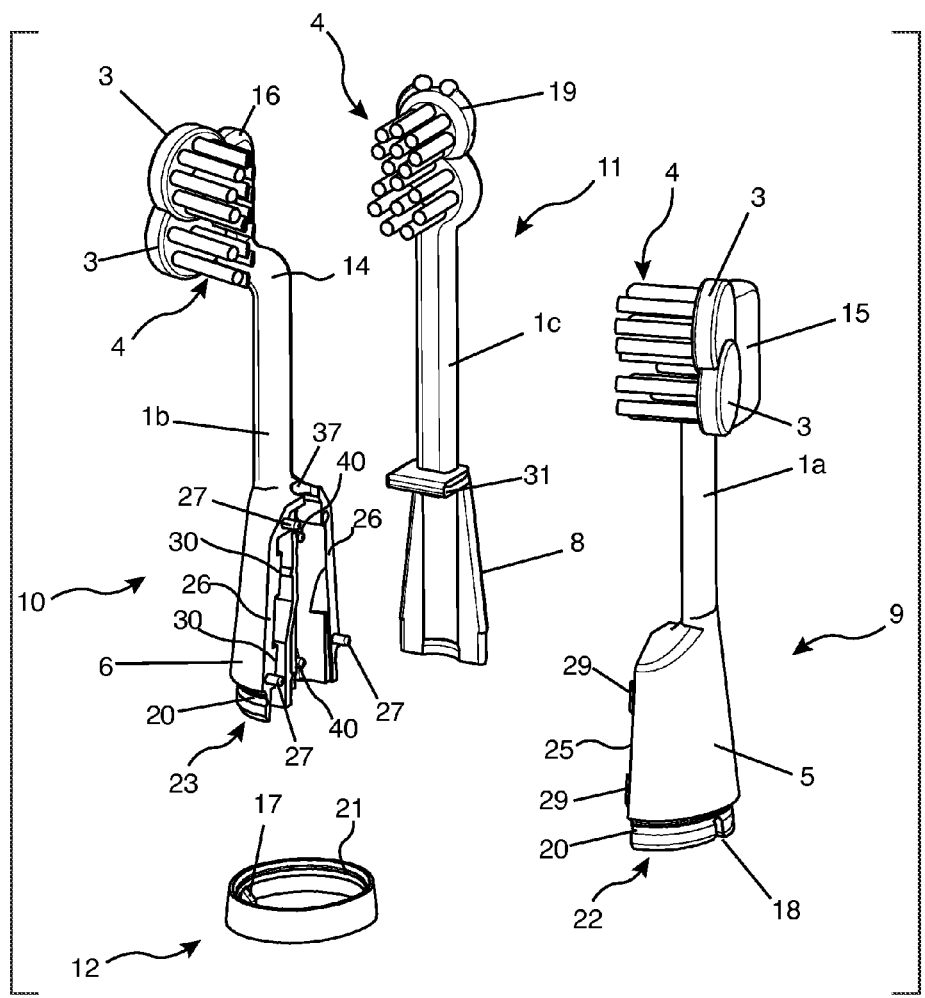
FIG. 8. Exploded view of certain embodiments of the invention.
Figure 9:
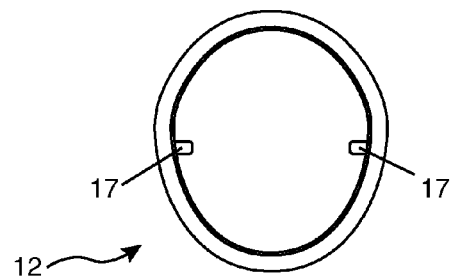
FIG. 9. Top-down view of a collar in certain embodiments of the invention.

As shown in FIG. 8, certain embodiments contain four components that include a plurality of components, including side components 9 and 10, a center component 11, and a collar 12. As those skilled in the art can appreciate side components 9 and 10 are on the left side and the right side of the center component 11. For the ease of description and not intended to be limiting, component 9 will be referred to hereinafter as a right component and component 10 will be referred to hereinafter as a left component. In certain embodiments, such right component 9 features a base 5, a neck 1a, a curved feature 13 and an upper portion 15 of a neck, and a rounded head 3, and such left component 10 includes a base 6, a neck 1b, a curved feature 14, an upper portion 16 of a neck, and a rounded head 3. A center component 11 includes a base 8, a neck 1c, and a head 19.

Still referring to FIG. 8, components of certain embodiments of the invention are attached, together with a collar 12. As shown in FIG. 1, FIG. 2, FIG. 3, FIG. 4, FIG. 5, FIG. 6, FIG. 7, and FIG. 8 a collar 12 fits around a lower aspect 22 of a right component 9, and a lower aspect 23 of a left component 10. Referring to FIG. 8, the lower aspects of a right component 9, and left component 10, include an undercut 20 that, when such components are assembled, form a continuous groove on the circumference of an assembled lower aspect. In certain embodiments, a collar 12, containing an overhang 21 forms a fit, such as a snap fit, with such continuous groove of an assembly. Further, in certain embodiments, a collar 12 further contains one or more protrusion 17 that fits with a depression 18 found on a right component 9 or a left component 10, as shown in FIG. 8, FIG. 9, FIG. 10, and FIG. 11.

Figure 7:
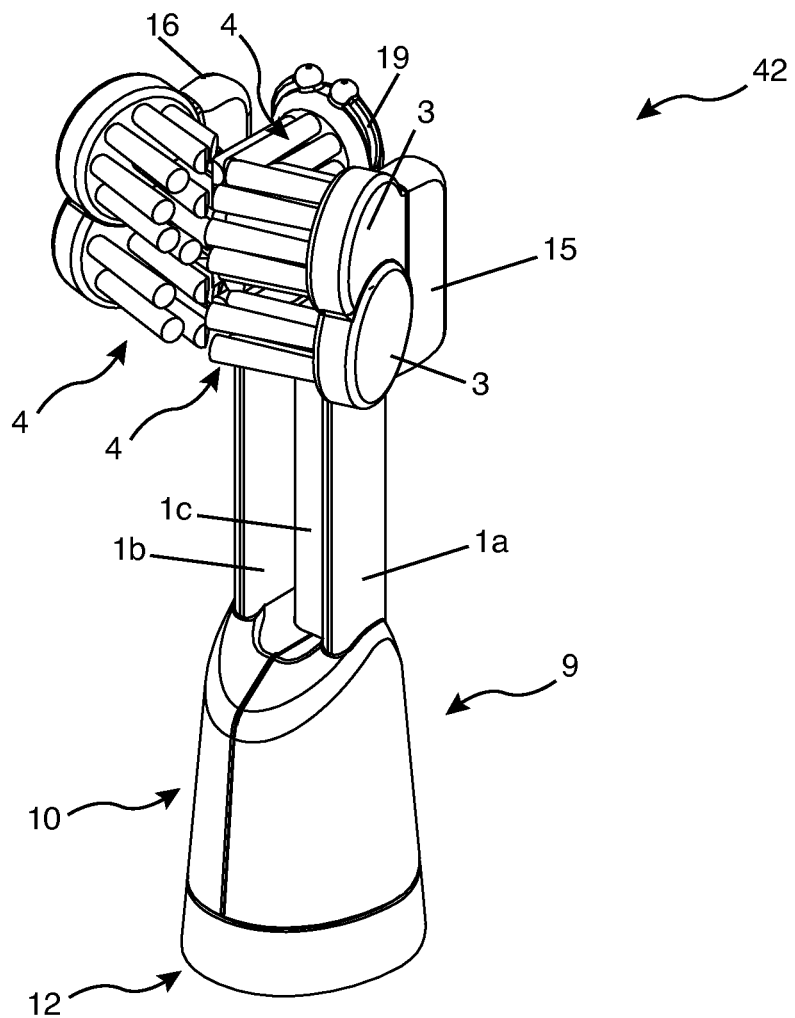
FIG. 7 Top angular view of a preferred embodiment of the invention.

In certain embodiments, as shown in FIG. 8, FIG. 10, and FIG. 11, attachment of the left component 10 and right component 9 is achieved by meeting of a left mating surface 26 and right mating surface 25. Alignment of such mating surfaces is achieved by pegs 27 found on one mating surface corresponding to, and fitting in holes 28 found on the opposite mating surface. Still referring to FIG. 8, FIG. 10, and FIG. 11, attachment of the left component 10 and right component 9 is attached with, for example, a snap fit, where a snapping member 29 found on a right component fits with an accepting member 30 found on a left component. In certain embodiments, portions of such components, for example, a left mating surface and right mating surface are further attached, for instance, with ultrasonic welding or adhesive. In general, in certain embodiments, as shown in FIG. 7, feature an assembly 42, where each component of such assembly has a motion that allows transmission of sonic vibration from a handle to individual heads.

In certain embodiments, a center component 11 fits within a cavity found in a left component 10 and right component 9, as shown in FIG. 8, FIG. 10, and FIG. 11. Referring to FIG.

12A and FIG. 12B, a center component 11 includes a tab 31 that fits in a crevice 32 of a right component 9 and a crevice 33 of a left component 10 shown in FIG. 10, and FIG. 11. Further, a portion of a base 8 of a center component 11 fits in a cavity 34 of a right component 9, and a cavity 35 of a left component 10. Additionally, a right component 9 has an indentation 36, and a left component 10 has an indentation 37 that has a form fitting a lower portion 38 of a neck 1c of the center component 11, as shown in certain embodiments in FIG. 8, FIG. 10, FIG. 11, FIG. 12A, and FIG. 12B. Moreover, alignment of a center component 11 to a left component 10 is achieved by, for example, holes 39 located on a base 8 of a center component 11 mating with pegs 40 found in left component 10, as shown in FIG. 8, FIG. 10, and FIG. 12B.

Referring to FIG. 1, FIG. 2, FIG. 3, FIG. 4, FIG. 5, FIG. 6, FIG. 7, FIG. 8, FIG. 9, FIG. 10, FIG. 11, FIG. 12A, FIG. 12B, FIG. 13, FIG. 14A, and FIG. 14B components and/or features of such components in certain embodiments of the invention include a high gloss polish. For example, certain features, such as a tab 31, overhang 21, or pegs 27 and 40 have a high gloss polish in certain embodiments. In certain embodiments a high gloss polish on surfaces of components and features of components allow for such surfaces to prevent trauma, scratching, or damage structures associated with a mouth, such as gums, teeth, etc.

Attachment of components as described in certain embodiments, allows such components having separate brushes to move individually. An advantage of such arrangement of such components is that each brush part acts independently to transmit energy from a handle, thus allowing sonic vibration from a handle to be transmitted into the head and neck regions as to allow cleaning action on the surface of teeth when certain embodiments of the invention are being used.

Certain embodiments of the invention, exemplified in an assembly 42 shown in FIG. 7, include a series of bristles 4. A rounded head 3 or a rounded head 19 is the attachment point for bristles 4, where such rounded head is affixed to an upper portion 15 of a neck of a right component 9, to an upper portion 16 of a neck of a left component 10, or a portion of a neck 1c of a center component 11. In certain embodiments, as shown in FIG. 1, FIG. 2, FIG. 3, FIG. 4, FIG. 5, FIG. 6 and FIG. 7, a series of bristles 4, attached to a rounded head, are oriented in three directions. The directions of such bristles allow three sides of teeth, including the buccal side, lingual side, and occlusal side to be cleaned simultaneously. Certain embodiments use nylon filaments such as DuPont Tynex® bristles. Certain embodiments incorporate the use of soft bristles or extra soft bristles. Such soft bristles having a diameter of 0.127 mm are effectively safe for use inside the mouth. They can prevent pinching and trauma, even if pressure is applied on the teeth and gum during use of such certain embodiments. In certain embodiments, such bristles 4 found on two adjacent components are spaced a distance 41, such as 2 mm apart, as shown in a top-down view in FIG. 13.

Embodiments of the present invention incorporate the benefits of a three-headed toothbrush, flexible neck regions, and the capability to deliver sonic action through the bristles. The present inventor has discovered that the flexible neck region available in prior art prevented the transmission of sonic motion to the bristles. As shown in certain embodiments in FIG. 1, FIG. 2, FIG. 3, FIG. 4, FIG. 5, FIG. 6 and FIG. 7, the neck of a right component 9, a left component 10 and a center component 11 neck are located between head and base portions. Certain embodiments of the present invention incorporate a rigid brush head material, such as plastic, in such a manner that allows the brush neck to flex with the contours of bodies of the mouth while still transmitting the energy necessary to facilitate the sonic motions of the brush. FIG. 5 and FIG. 6 disclose rounded heads 3 that incorporate means to transmit sonic or spinning energy to the bristles of the brush. It will be appreciated that parts of certain embodiments of the invention are may comprise of one or more materials, where examples of materials include but are not limited to materials polymeric, metallic, and/or organic in nature. In certain embodiments, the components are created by injection molding using plastic, where such exemplary plastic include acrylonitrile butadiene styrene (ABS).

Embodiments of the present invention include a head and neck region that is removable from the handle, allowing an economical change to a fresh toothbrush head when the bristles become worn. In certain embodiments, the head and neck regions are attached to a handle with a friction grip. A friction grip allows a sonic movement from a handle to be transferred to the pieces in the head and neck regions. As shown in FIG. 3, a cavity 2 that is created when the right, left, and center components are assembled provides a way to attach certain embodiment of the invention to a brush head handle. As shown in FIG. 14A and FIG. 14B, in certain embodiments, a protruding portion 43 of a handle 44 fit within a cavity 2 formed by an assembly 42. Similarly, the head and neck unit of an embodiment of the present invention can be made to fit onto multiple types of handles.

While various embodiments of the present invention have been described in detail, it is apparent that modifications and alterations of those embodiments will occur to those skilled in the art. However, it is expressly understood that such modifications and alterations are within the scope and spirit of the present invention, as set forth in the following claims. Further, the invention(s) described herein are capable of other embodiments and being practiced or of being carried out in various ways. In addition, it is to be understood that the phraseology and terminology used herein is for the purposes of description and should not be regarded as limiting. The use of "including," "comprising," or "adding," and variations thereof herein are meant to encompass the items listed thereafter and equivalents thereof, as well as, additional items.

What is claimed is:

1. An apparatus for cleaning teeth comprising:
    a bristle assembly comprising:
        a first component comprising a first base, a first neck, and a first head having first bristles;
        a second component comprising a second base, a second neck, and a second head having second bristles;
        a third component comprising a third base, a third neck, and a third head having third bristles, wherein each of the first neck, the second neck, and the third neck flexes independently of each other; and
    a powered handle component removably coupled to the first base, the second base, and the third base that transmits energy to at least one of the first, second, and third bristles.

2. The apparatus of claim 1, wherein a first distance between the first bristles and the second bristles and a second distance between the second bristles and the third bristles allow vibration for cleaning.

3. The apparatus of claim 2, wherein the first distance and the second distance are two millimeters.

4. The apparatus of claim 1, wherein the first, second, and third components comprise acrylonitrile butadiene styrene.

5. The apparatus of claim 1, wherein the first, second, and third bristles have a diameter of 0.127 millimeters.

6. The apparatus of claim 2, wherein the first, second, and third bristles have a diameter of 0.127 millimeters.

7. The apparatus of claim 1, wherein the energy causes sonic movement of at least one of the first, second, and third bristles.

8. The apparatus of claim 7, wherein the sonic movement comprises sonic vibrations.

9. The apparatus of claim 1, wherein the energy causes spinning movement of at least one of the first, second, and third bristles.

10. The apparatus of claim 1, further comprising a collar component configured to secure the first component, the second component, and the third component.

11. The apparatus of claim 10, wherein the collar component comprises a groove that forms a snap fit around the first base, the second base, and the third base.

12. The apparatus of claim 1, wherein the first component comprises a snapping component that snaps into an accepting component of the second component.

13. The apparatus of claim 1, wherein the third component comprises a tab that fits into a first crevice of the first component and a second crevice of the second component.

14. The apparatus of claim 1, wherein the bristle assembly forms a cavity and the powered handle component comprises a protruding portion that fits within the cavity.

15. A bristle assembly comprising:
   a first component comprising a first base, a first neck, and a first head having first bristles;
   a second component comprising a second base, a second neck, and a second head having second bristles; and
   a third component comprising a third base, a third neck, and a third head having third bristles, wherein
      each of the first neck, the second neck, and the third neck flexes independently of each other, and
      the first component, the second component, and the third component are coupled together so as to form a cavity configured to receive energy from a powered handle.

16. The bristle assembly of claim 15, wherein a first distance between the first bristles and the second bristles and a second distance between the second bristles and the third bristles allow vibration for cleaning.

17. The bristle assembly of claim 16, wherein the first distance and the second distance are two millimeters.

18. The bristle assembly of claim 15, wherein the first base, the second base, and the third base transmit vibrations received from the powered handle to the first, the second, and the third bristles.

19. The bristle assembly of claim 15, further comprising a collar component configured to secure the first component, the second component, and the third component.

20. The bristle assembly of claim 19, wherein the collar component comprises a groove that forms a snap fit around the first base, the second base, and the third base.

* * * * *